(12) United States Patent
McKee et al.

(10) Patent No.: US 9,945,809 B2
(45) Date of Patent: Apr. 17, 2018

(54) DRY PROTEIN TRANSFER

(71) Applicant: Bio-Rad Laboratories, Inc., Hercules, CA (US)

(72) Inventors: Clayton T. McKee, Davis, CA (US); Steve Swihart, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 164 days.

(21) Appl. No.: 15/019,792

(22) Filed: Feb. 9, 2016

(65) Prior Publication Data

US 2016/0231272 A1    Aug. 11, 2016

Related U.S. Application Data

(60) Provisional application No. 62/114,387, filed on Feb. 10, 2015.

(51) Int. Cl.
*G01N 27/447* (2006.01)
*G01N 27/453* (2006.01)

(52) U.S. Cl.
CPC ............................. *G01N 27/44739* (2013.01)

(58) Field of Classification Search
CPC ............................................... G01N 27/44739
See application file for complete search history.

(56) References Cited

U.S. PATENT DOCUMENTS

| 4,840,714 | A | * | 6/1989 | Littlehales | G01N 27/44739 |
| | | | | | 204/464 |
| 7,899,552 | B2 | | 3/2011 | Atanasoska, II et al. | |
| 8,192,601 | B2 | * | 6/2012 | Latham | B01D 57/02 |
| | | | | | 204/456 |
| 8,394,250 | B2 | | 3/2013 | Margalit et al. | |
| 2010/0044229 | A1 | | 2/2010 | Margalt et al. | |

FOREIGN PATENT DOCUMENTS

| EP | 2151501 A1 * | 7/2008 | ............... C12Q 1/24 |
| EP | 2398819 B1 | 7/2014 | |
| JP | 2014-225617 A * | 12/2014 | ............ H01G 11/22 |
| WO | 1997/012680 A2 | 4/1997 | |
| WO | WO 9736170 A1 * | 10/1997 | ............ G01N 27/26 |
| WO | 2005/029055 A1 | 3/2005 | |

OTHER PUBLICATIONS

JPO computer-generated English language translation of Maruyama Tsukasa JP 2014-225617 A. 2017. Patent published Dec. 4, 2014. Downloaded Sep. 14, 2017. Patent published Dec. 4, 2014.*
Erlandsson, Per, G., et al., "Electrolysis-reducing electrodes for electrokinetic devices," Electrophoresis, 2011, vol. 32, pp. 784-790.
Bengtsson, Katarina, et al., "Conducting Polymer Electrodes for Gel Electrophoresis," PLOS ONE, Feb. 2014, vol. 9, Issue 2, e89416, 5 pages.

(Continued)

*Primary Examiner* — Alexander S Noguerola
(74) *Attorney, Agent, or Firm* — Kilpatrick Townsend Stockton LLP

(57) ABSTRACT

Kits, systems, and methods are provided for transferring biological macromolecules from an electrophoresis slab gel to a blotting membrane using conductive polymer electrodes.

19 Claims, 4 Drawing Sheets

(56) References Cited

OTHER PUBLICATIONS

Chen, C., et al., "Electrical conductivity of polymer blends of poly (3,4-ethylenedioxythiophene): Poly (styrenesulfonate): N-methyl-2-pyrrolidinone and polyvinyl alcohol," Journal of Applied Polymer Science, Feb. 1, 2012, pp. 3134-3141.
Paul, D.R., et al., "Polymer nanotechnology: nanocomposites," Polymer, 2008, vol. 49, No. 15, pp. 3187-3204.
Uddin, F., "Studies in Finishing Effects of Clay Mineral in Polymers and Synthetic Fibers," Advances in Materials Science and Engineering, 2013.
International Search Report and Written Opinion dated May 6, 2016 in PCT/US16/17164, 11 pages.
Paul, D.R. et al.; "Polymer nanotechnology: Nanocomposites"; *Polymer*; vol. 49; pp. 3187-3204.

\* cited by examiner

DRY PROTEIN TRANSFER

CROSS-REFERENCE TO RELATED PATENT APPLICATIONS

The present application claims benefit of priority to U.S. Provisional Patent Application No. 62/114,387, filed Feb. 10, 2015, which is incorporated by reference.

BACKGROUND OF THE INVENTION

Proteins, nucleic acids, or other biological species that have been electrophoretically separated in a slab gel are often transferred to a blotting membrane formed of nitrocellulose, nylon, polyvinyl difluoride, or similar materials prior to identification and quantification. A common transfer technique is electroblotting, in which flat surfaces of the gel and membrane are placed in direct contact. An electric current is then passed through both the gel and the membrane in a transverse direction, thereby transferring the species in a manner similar to that by which the species were mobilized within the gel. When the species are DNA fragments, the transfer is termed a Southern blot after its originator, the British biologist Edwin M. Southern. By analogy, the transfer of RNA fragments is termed northern blotting, and the transfer of proteins or polypeptides is termed western blotting. Still further examples are "eastern" blots for post-translational modifications, and "far western" blots for protein interactions.

Electroblotting can be performed in either a wet, dry, or semi-dry format. In wet blotting, the gel and membrane are layered over each other in a stack which is immersed in a transfer buffer solution in a tank on whose walls are mounted wire or plate electrodes. The electrodes are then energized to cause the solutes to migrate from the gel to the membrane. In semi-dry blotting, filter papers wetted with the transfer buffer solution are placed on the top and bottom of the stack with the gel and the membrane in between to form a "blotting sandwich." The electrodes are then placed in direct contact with the exposed surfaces of the wetted filter papers. In dry electroblotting, no liquid buffers are used other than those residing in the gels. Descriptions of wet, dry, and semi-dry electroblotting and the associated materials and equipment are found in Margalit et al. (Invitrogen) United States Patent Application Publications No. US 2006/0272946 A1 (Dec. 7, 2006), No. US 2006/0278531 A1 (Dec. 14, 2006), and No. US 2009/0026079 A1 (Jan. 29, 2009); Littlehales (American Bionetics) U.S. Pat. No. 4,840,714 (Jun. 20, 1989); Dyson et al. (Amersham International) U.S. Pat. No. 4,889,606 (Dec. 26, 1989); Schuette (Life Technologies, Inc.), U.S. Pat. No. 5,013,420 (May 7, 1991); Chan et al. (Abbott Laboratories), U.S. Pat. No. 5,356,772 (Oct. 18, 1994); Camacho (Hoefer Scientific Instruments), U.S. Pat. No. 5,445,723 (Aug. 29, 2005); Boquet (Bertin & Cie), U.S. Pat. No. 5,482,613 (Jan. 9, 1996); and Chen (Wealtec Enterprise Co., Ltd.) U.S. Pat. No. 6,592,734 (Jul. 15, 2003).

In all electroblotting formats, one or more aqueous solutions contact or are contained within the electrophoresis gel or blotting membrane. When metal (e.g., platinum, silver, lead, copper, or aluminum) electrodes are used for electroblotting, electrochemical reactions occur at the interface of each electrode with these solutions. The reactions can involve water electrolysis, producing $O_2$ gas, hydrogen ions, and hydrogen peroxide at the anode, and $H_2$ gas and hydroxide ions at the cathode. Electrochemical reactions can also ionize the electrodes, causing metal ions to be released from the surface of an electrode into the adjacent solution. The products of such reactions can interact with biological species undergoing transfer between the electrophoresis gel and blotting membrane, rendering these species chemically modified (e.g., oxidized or reduced), denatured, or nonfunctional. Electrochemical reaction products, especially gases produced by water electrolysis, can also reduce the surface area of electrodes available to transmit current and make electroblotting less efficient.

SUMMARY OF THE INVENTION

Kits, systems, and methods are provided for transferring biological macromolecules from an electrophoresis slab gel to a blotting membrane by electroblotting.

In a first aspect of the present invention, a kit is provided. The kit comprises two conductive polymer electrodes, wherein each electrode comprises a matrix and a terminal. The matrix comprises a conductive polymer blend, which comprises a conjugated organic polymer. The terminal is electrically coupled to the matrix, and is configured to receive electrical power from a power supply.

In some embodiments of the kit, the conjugated organic polymer is a polythiophene, polyaniline, polypyrrole, polyphenylene, or poly(p-phenylene vinylene). The conjugated organic polymer can be poly(3,4-ethylenedioxythiophene) (PEDOT). In some embodiments, the conductive polymer blend further comprises a polyelectrolyte. In these embodiments, the conjugated organic polymer can be positively charged and the polyelectrolyte can be negatively charged. The polyelectrolyte can be water-soluble and/or a sulfonated polystyrene. The conductive polymer blend can comprise poly(3,4-ethylenedioxythiophene):poly(styrenesulfonate) (PEDOT:PSS).

In some embodiments of the kit, the conductive polymer blend is water-soluble. In some embodiments, the conductive polymer blend has a conductivity of at least 0.1, 1, 10, or 100 S/cm. In some embodiments, the matrix is a nanocomposite and can further comprise a synthetic clay. In some embodiments, the matrix is thixotropic. In some embodiments, the matrix has a conductivity of at least 0.1, 1, 10, or 100 S/cm. In some embodiments, the conductive polymer blend makes up at least 0.1, 0.3, 1, 1.3, 3, 10, or 30 percent of the weight of the matrix. In some embodiments, the matrix further comprises a porous substrate in which the conductive polymer blend is disposed.

In some embodiments of the kit, each electrode further comprises a rigid cassette encasing the matrix. The cassette comprises a floor, walls connected to the floor, and a lip extending laterally from the walls. The floor and walls of the cassette define a central cavity, and the matrix is disposed in the central cavity. In these embodiments, at least one electrode can further comprise a protective sheet adhering to the lip of the cassette and covering the central cavity, and the protective sheet is configured to be removed from the lip to expose the central cavity. At least one electrode can further comprise a porous membrane mounted to the matrix or the lip of the cassette and covering the matrix. The terminal of each electrode can be disposed on an external surface of the cassette and be electrically coupled to the matrix through a conductive member, which passes through a wall of the cassette or the floor of the cassette.

In embodiments of the kit, at least one electrode can further comprise a conductive plate disposed between the matrix and the floor of the cassette, wherein the conductive plate is electrically coupled to the matrix and the terminal. The cassette can comprise an electrically insulating material. The lips of the cassettes can be positioned to engage each other when the electrodes are brought together, and the lip of one cassette can be complementary in shape to the lip of the other cassette, so that engagement of the lips of the cassettes secures the electrodes together while leaving a gap between the matrices.

In some embodiments of the kit, a plurality of alignment pegs protrude from the lip of the cassette of at least one electrode, a plurality of alignment holes are cut into the lip of the cassette of at least one electrode, the alignment pegs and alignment holes are positioned to engage each other when the electrodes are brought together, and the alignment holes are complementary in shape to the alignment pegs, so that engagement of the alignment pegs with the alignment holes secures the electrodes together while leaving a gap between the matrices. In these embodiments, an electrically insulating material can be disposed on the surface of each alignment peg, or an electrically insulating material can line the interior of each alignment hole.

Some embodiments of the kit further comprise a clamp for securing the two electrodes together around an electrophoresis slab gel and a blotting membrane. When the electrodes are so secured, the matrices of the electrodes face each other and are parallel; the electrophoresis slab gel and the blotting membrane are accommodated in a gap between the two electrodes; and the clamp exerts force on the electrodes to keep each electrode in contact with either the electrophoresis slab gel or the blotting membrane, and keep the electrophoresis slab gel and blotting membrane in contact with each other. In these embodiments, the clamp can be electrically coupled to the terminal of each electrode and can be configured to deliver electrical power to the terminals from the power supply.

In some embodiments, the kit further comprises a power supply configured to deliver electrical power to the electrodes through the terminals, wherein the current delivered to one electrode is of opposite polarity from the current delivered to the other electrode.

In a second aspect of the invention, a system is provided for transferring biological macromolecules from an electrophoresis slab gel to a blotting membrane by electroblotting. The system includes: the two conductive polymer electrodes of the kit described above; an electrophoresis slab gel and a blotting membrane accommodated in a gap between the electrodes; and a power supply configured to deliver electrical power to the electrodes through the terminals, wherein the current delivered to one electrode is of opposite polarity from the current delivered to the other electrode. The system is configured to transfer biological macromolecules from the electrophoresis slab gel to the blotting membrane, in the absence of an exogenous source of buffer, electrolyte, or solvent in contact with the electrophoresis slab gel or blotting membrane, upon delivering electrical power to the electrodes.

In some embodiments, the system further comprises a clamp for securing the two electrodes together around the electrophoresis slab gel and the blotting membrane, such that, when the electrodes are so secured: the matrices of the electrodes face each other and are parallel; and the clamp exerts force on the electrodes to keep each electrode in contact with either the electrophoresis slab gel or the blotting membrane, and keep the electrophoresis slab gel and blotting membrane in contact with each other. In these embodiments, the clamp can be electrically coupled to the terminal of each electrode and can be configured to deliver electrical power to the terminals from the power supply.

In a third aspect of the present invention, a method is provided for transferring biological macromolecules from an electrophoresis slab gel to a blotting membrane by electroblotting. The electrophoresis slab gel and the blotting membrane are accommodated in a gap between two conductive polymer electrodes of the kit described above, such that each electrode is in contact with either the electrophoresis slab gel or the blotting membrane, and the electrophoresis slab gel and blotting membrane are in contact with each other. In addition, the terminals of the electrodes are connected to a power supply. The method comprises delivering electrical power to the electrodes through the terminals, wherein the current delivered to one electrode is of opposite polarity from the current delivered to the other electrode, thereby transferring biological macromolecules from the electrophoresis slab gel to the blotting membrane by electroblotting.

In some embodiments, the method further comprises securing the two electrodes together. In some embodiments of the method, no exogenous source of buffer, electrolyte, or solvent is in contact with the electrophoresis slab gel or blotting membrane.

DETAILED DESCRIPTION OF THE INVENTION

I. Introduction

It has now been discovered that efficient electroblotting of proteins and other biological species can be carried out using conductive polymer electrodes. Each electrode includes a conjugated organic polymer that can be oxidized or reduced upon application of an external electrical potential. The conjugated organic polymer is part of a conductive polymer blend such as PEDOT:PSS that not only conducts current, but also serves as a source or sink of electrophoretically migrating ions. These ions can penetrate the electrodes, associating with or dissociating from the conductive polymer blend as the oxidation state of the conjugated organic polymer changes. Due to the movement of solution ions into and out of the electrodes, and the free movement of charges (e.g., electrons) within the electrodes, electrochemical reactions are less prevalent on the electrode surfaces as compared with metal electrodes. Thus, complications of electroblotting arising from water electrolysis or electrode dissolution are mitigated.

In some embodiments of the present invention, each conductive polymer electrode includes a nanocomposite matrix of which the conductive polymer blend is one component. Other components can physically bridge polymer molecules and/or confer strength upon the matrix. Thus, the matrix can have a solid, semi-solid, or thixotropic body and/or a planar surface. A polymer electrode can also employ a rigid cassette to encase the matrix, and a terminal electrically coupled to the matrix to supply power. Kits, systems, and methods are provided herein for transferring biological macromolecules from electrophoresis gels to membranes using conductive polymer electrodes.

II. Kits

Figure 1:
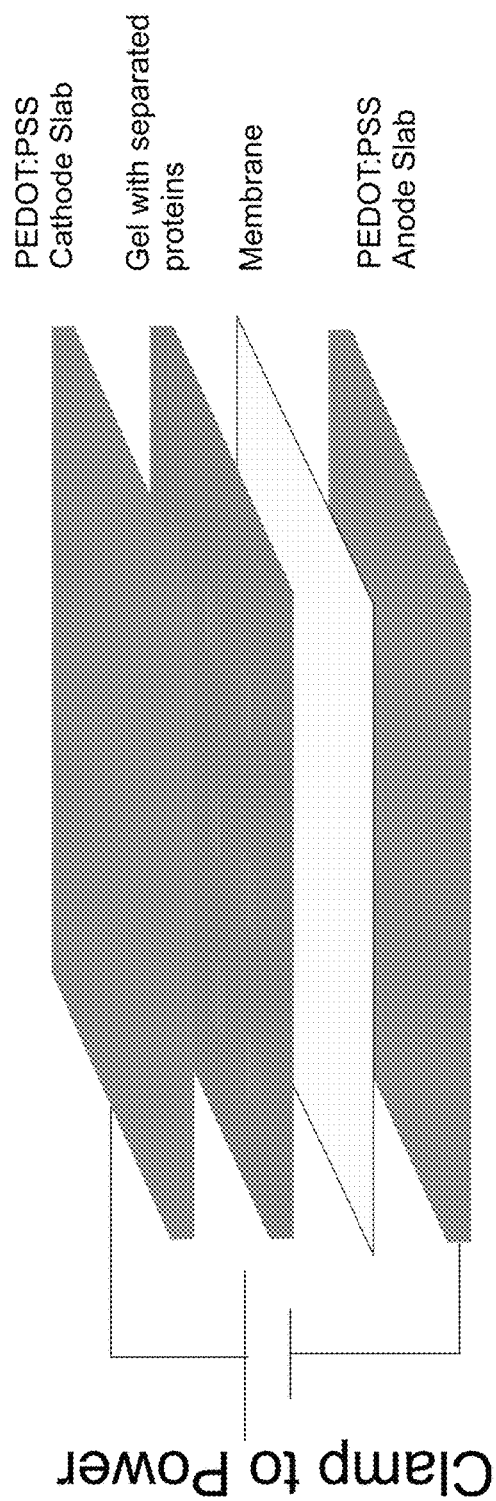
FIG. 1 is a schematic depiction of an electrophoresis slab gel and a blotting membrane sandwiched between two conductive polymer electrodes, according to some embodiments of the invention.

Kits as described herein include two conductive polymer electrodes (also referred to as "polymer electrodes" or simply "electrodes"), each of which includes a matrix and a terminal. The matrix includes a conductive polymer blend, and the terminal is electrically coupled to the matrix. The matrix can have at least one planar surface to contact or otherwise electrically interface with an electrophoresis gel or blotting membrane placed in proximity to the matrix (FIG. 1). This planar surface can have dimensions comparable to or exceeding those of gels and membranes commonly used in the art. The terminal of each electrode is configured to receive electrical power from a power supply. Through the terminals, the power supply can be used to supply or withdraw current from the matrices of the electrodes, or establish a flow of current and/or a potential difference between the matrices, for electroblotting.

The conductive polymer blend in the matrix of each electrode includes a conjugated organic polymer. Examples of conjugated organic polymers that can be used in embodiments of the present invention include polythiophenes, polyanilines, polypyrroles, polyphenylenes, or poly(p-phenylene vinylene)s. In some embodiments, the conjugated organic polymer is poly(3,4-ethylenedioxythiophene) (PEDOT), a polythiophene. Conjugated organic polymers used herein can have any desired chain lengths, branching, substituents, heteroatoms, or pendant moieties. The matrix of each conductive polymer electrode can include a single conjugated organic polymer, or multiple conjugated organic polymers in desired proportions. The same conjugated organic polymer(s) can be used in the matrices of the two electrodes, or different conjugated organic polymers (or combinations thereof) can be used.

In some embodiments, the conductive polymer blend also includes a polyelectrolyte, which can increase the stability, solubility, and/or conductivity of the conductive polymer blend. Useful polyelectrolytes include water-soluble polyelectrolytes such as sulfonated polystyrenes (e.g., poly(styrenesulfonate) or poly(styrene sulfonic acid), both known as PSS). Methods of polymerizing PEDOT in aqueous PSS are known in the art and are described in, for example, Groenendaal et al., *Advanced Materials* 12, pp. 481-494, 2000. The polyelectrolyte can act as a charge-balancing dopant, providing negative charges to counter positive charges on the conjugated organic polymer. Thus, the conductive polymer blend can exist as an organic salt and in some embodiments is water-soluble. In some embodiments, the conductive polymer blend comprises poly(3,4-ethylenedioxythiophene):poly(styrenesulfonate) (PEDOT:PSS).

The conductive polymer blend can be prepared as desired, or can be obtained commercially. Aqueous dispersions of PEDOT:PSS are available from Sigma-Aldrich Corporation (St. Louis, Mo., USA), and proprietary formulations of PEDOT:PSS are available from Agfa-Gevaert N.V. (Mortsel, Belgium) under the trade name ORGACON™. In some embodiments, PEDOT polymerization occurs under oxidizing (i.e., p-doping) conditions and includes an oxidizing agent such as sodium persulfate. Other reagents can be used at various times to enhance the conductivity of the conductive polymer blend, as described for example in: Jönsson et al., *Synthetic Metals* 139, pp. 1-10, 2003; Ouyang et al., *Polymer* 45, pp. 8443-8450, 2004; and Fan et al., *Macromolecules* 41, pp. 5971-5973, 2008. These reagents can be added to a polymerization reaction used to prepare the conductive polymer blend (for example, as a secondary dopant), added to a solution in which the conductive polymer blend is suspended or dispersed, or used to treat the conductive polymer blend in solid or dried form. Examples of conductivity-increasing reagents include ethylene glycol, polyethylene glycol, dimethyl sulfoxide, sorbitol, methylpyrrolidone, isopropanol, dimethylformamide, glycerol, 2-nitroethanol, and various ionic and anionic surfactants. In some embodiments, the conductive polymer blend has a conductivity of at least 0.1, 1, 10, or 100 S/cm.

The matrix of each conductive polymer electrode can be liquid or solid, and can have any desired consistency. For example, the matrix can be a putty, paste, gel, or slurry. The matrix can adopt a slab shape as shown in FIG. 1, or any other shape that is useful for electroblotting. In some embodiments, the matrix is a nanocomposite and includes one or more nanoscale materials in addition to the conductive polymer blend. One such nanoscale material is synthetic exfoliated clay, which is available from BYK-Chemie GmbH (Wesel, Germany) under the trade name LAPONITE®. Exfoliated clay is thought to bridge the polymer chains within the conductive polymer blend and mediate the rheology of the matrix. Other useful nanoscale materials include gold, silver, and nickel nanoparticles; various silicas and silicates (e.g., fumed silica and silica gel); organic polymers (e.g., nonionic organic polymers and block copolymers); carbon nanotubes; electrospun fibers; and dendrimers (e.g., poly(amidoamine)). Nanocomposite matrices can be prepared using inorganic materials, organic materials, or both. Nanoscale materials generally can confer desired physical properties on the matrix, such as: increased mechanical stiffness or strength; increased or decreased viscosity; thixotropy; or increased conductivity. In some embodiments, the matrix is thixotropic. In some embodiments, nanoscale materials bridge or crosslink conjugated organic polymer and/or polyelectrolyte molecules within the matrix.

The matrix can also be prepared by adding the conductive polymer blend to a thickening agent such as gelatin, agarose, or acrylamide. Useful thickening agents also include polysaccharides and other organic polymers. As a result of gelation, crosslinking, aggregation, agglomeration, or polymerization of the thickening agent, the matrix can be more viscous or solid than the conductive polymer blend alone (or, for example, an aqueous suspension thereof). In some embodiments, the matrix, including the conductive polymer blend, nanoscale materials, thickening agent, or other components, has a conductivity of at least 0.1, 1, 10, or 100 S/cm. The conductive polymer blend can be mixed with nanoscale materials or other components in any desired proportions. In some embodiments, the conductive polymer blend makes up at least 0.1, 0.3, 1, 1.3, 3, 10, or 30 percent of the weight of the matrix.

The matrix can also include a porous substrate in which the conductive polymer blend is disposed. The porous substrate can be a piece of material such as sponge, paper (e.g. Whatman paper), membranous material, or ceramic that can absorb a liquid. Thus, when the conductive polymer blend is in liquid or semi-liquid form (for example, when part of an aqueous dispersion), the porous substrate can be soaked or injected with the conductive polymer blend and provide mechanical support to the conductive polymer blend. In other embodiments, the matrix includes a solid substrate on which the conductive polymer blend is coated or deposited, for example as a film. Materials such as glass, ceramic, plastic, or metal can be used for the solid substrate. If appropriate, the solid substrate can have a planar surface congruent to that of an electrophoresis gel or blotting membrane. A porous and/or solid substrate can generally be used to confer shape on the matrix of a conductive polymer electrode and ensure that the electrode has a geometry useful for electroblotting. In some embodiments, the conductive polymer blend hardens or becomes less flowable upon addition to a porous or solid substrate. As desired, the substrate can be electrically conductive or insulating.

Embodiments of the matrix that include water or another solvent can be provided to the end user in wet or dry form. If in wet form, the solvent is added to the matrix at the time of manufacture. Thus, the end user can conveniently use the conductive polymer electrodes in a kit without modification. If the matrix is instead provided in dry form, the user can add some or all of the solvent at the point of use. Adding the solvent can involve, for example, mixing the conductive polymer blend and other components of the matrix with the solvent, injecting the solvent into a porous substrate in which the conductive polymer blend is disposed, or pipetting the solvent onto a solid substrate on which the conductive polymer blend is coated. Providing the matrix in dry form can prolong the shelf life of the matrix by preventing solution-phase side reactions between the conjugated organic polymer and other components of the matrix. If desired, an aliquot of the solvent (for example, an aqueous buffer) can be supplied to the end user along with the matrix. This aliquot can have a volume chosen so that the solvent and conductive polymer blend are combined in a fixed proportion. The volume, pH, or composition of the solvent to be added can also be adjusted to impart desired physical properties to the matrix. For example, a smaller volume of solvent can be added to the matrix of one electrode to make the matrix more viscous. A solvent containing a higher salt (e.g., NaCl or KCl) concentration can be added to facilitate larger currents during electroblotting.

The kits disclosed herein also include one or more rigid cassettes in some embodiments. Each cassette is configured to encase the matrix of a conductive polymer electrode and provide mechanical support to the matrix. Thus, the cassette can supplement the support provided by any porous or solid substrate. The cassette can also protect the matrix when not in use (for example, during shipping and prior to use) from mechanical deformation, contamination with foreign materials, and other hazards. Each cassette comprises a floor, walls connected to the floor, and a lip extending laterally from the walls. While many geometries of the cassette are possible, in some embodiments the walls are perpendicular to the floor, or the lip is perpendicular to the walls or parallel to the floor. The floor and walls of the cassette define a central cavity in which the matrix of the conductive polymer electrode is disposed. The cassette can include or be made of an electrically insulating material such as ceramic or plastic.

Figure 2:
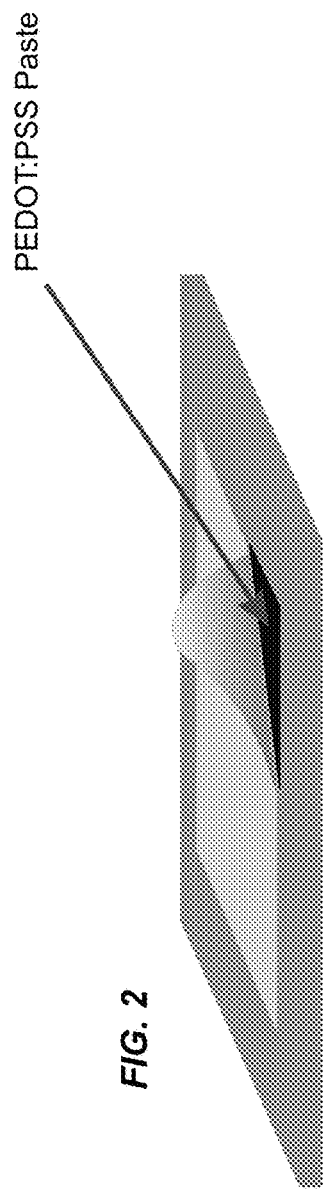
FIG. 2 shows a conductive polymer electrode comprising a rigid cassette and a protective sheet adhering to a lip of the cassette. The example electrode consumable depicts a past of PEDOT:PSS enclosed in a rigid cassette. A self-adhesive covers the paste and can be removed from the consumable so that contact between the gel and electrode is created before the electrophoretic transfer.

In some embodiments, the cassette is open on one side to provide an interface between the matrix and a electrophoresis gel or blotting membrane used in electroblotting. The exposed portion of the matrix can be a planar surface as discussed above. In some embodiments, a protective sheet is included in the kit for at least one of the conductive polymer electrodes. The protective sheet adheres to the lip of the cassette and covers the central cavity as well as the matrix inside the cassette (FIG. 2). The protective sheet is configured to be removed from the lip to expose the central cavity, thereby exposing the matrix (or a portion or surface thereof) to the space outside the cassette. Thus, the protective sheet can protect the matrix from contamination at times when it is not in use (for example, when the conductive polymer electrode is being transported or stored prior to use). Alternatively or in addition, in some embodiments at least one electrode includes a porous membrane mounted to the matrix or the lip of the cassette. The porous membrane covers the matrix on the side that can electrically interface with an electrophoresis gel or blotting membrane, and can physically separate the matrix from these elements during electroblotting. The porous membrane nevertheless allows current to flow between the two conductive polymer electrodes through the electrophoresis gel and blotting membrane. If desired, the porous membrane can be soaked with a conductive liquid such as water or a buffer solution, or made of a conductive material such as metal. In some embodiments, the porous membrane seals the matrix inside the cassette, so that no part of the matrix is directly exposed to the space outside the cassette. In some embodiments, at least one conductive polymer electrode includes both a porous membrane and a protective sheet, in which case the porous membrane is layered between the protective sheet and the matrix.

Figure 3:
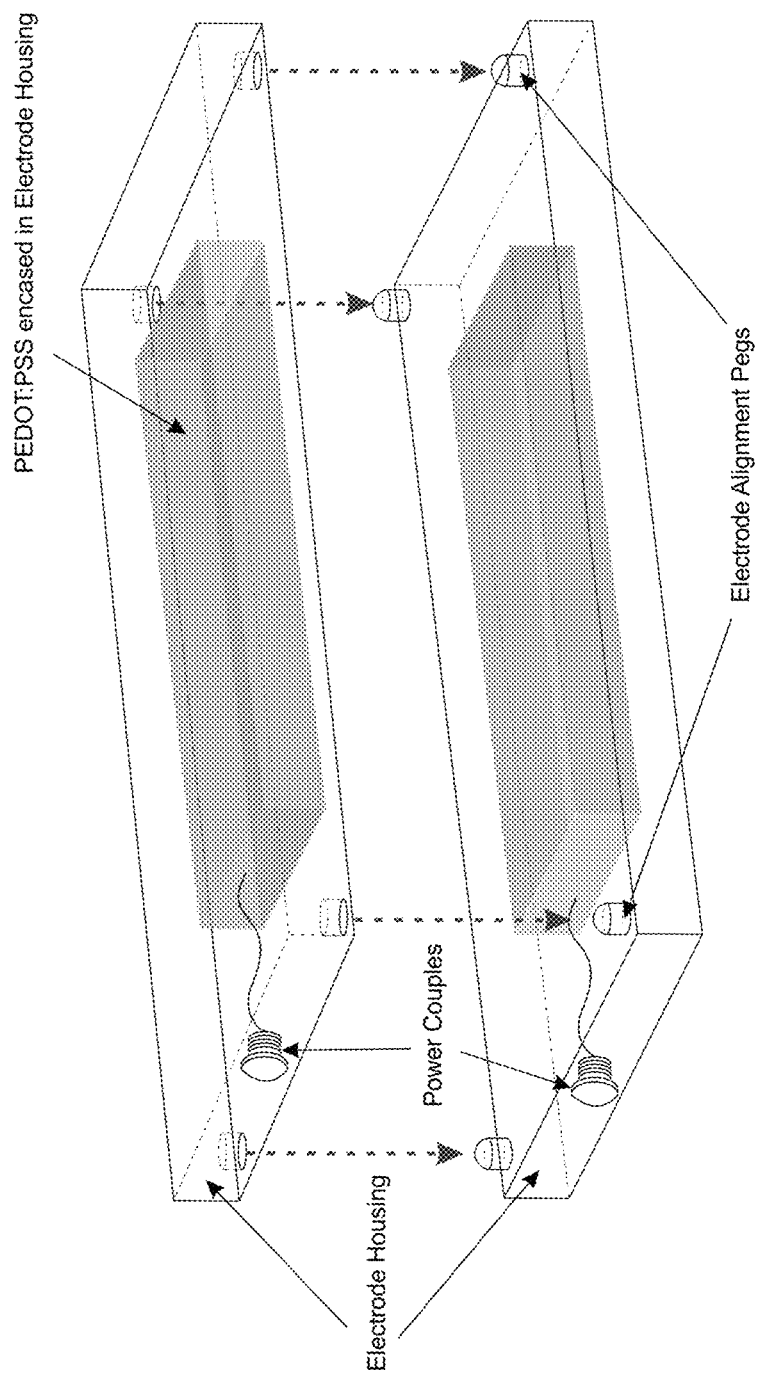
FIG. 3 shows conductive polymer electrodes according to some embodiments of the invention. The matrix of each electrode includes a PEDOT:PSS conductive polymer blend and is encased in a rigid cassette. Alignment pegs protrude from the lip of the cassette of the lower electrode, and alignment holes are cut into the lip of the cassette of the upper electrode. The terminal of each electrode is disposed on an external surface of the cassette and is electrically coupled to the matrix through a wire.

The cassette can also support a mechanical coupling between the matrix and the terminal of a conductive polymer electrode (FIG. 3). In some embodiments, the terminal is disposed on an external surface of the cassette and is electrically coupled to the matrix through a conductive member. The conductive member can pass through a wall of the cassette or the floor of the cassette. Thus, the wall or floor can include a hole or passage to accommodate the conductive member while otherwise keeping the matrix separated from the space outside the cassette. Examples of conducting members include copper, silver, gold, and platinum wires, which can optionally be electrically insulated (such as with polymeric cladding) prior to insertion in the cassette. The terminal can have a shape suitable for connection to a power supply for electroblotting. For example, the terminal can be shaped to connect to one or more wires with banana plugs or alligator clips.

In some embodiments, the matrix and terminal of a conductive polymer electrode are electrically coupled to each other within the cassette by way of a conductive plate. The conductive plate can be made of any convenient electrically conductive material, such as copper, silver, gold, platinum, another metal, or a metal alloy. The conductive plate is disposed between the matrix and the floor of the cassette and is therefore physically separated from any electrophoresis gel or blotting membrane used in electroblotting. In some embodiments, the conductive plate is on an opposite side of the matrix from a porous membrane or protective sheet adhering to the lip of the cassette.

The conductive plate can be held in contact with the matrix by friction or pressure, or can be affixed to the matrix using, for example, an electrically conductive adhesive. The conductive plate can alternatively be bonded directly to the matrix, or coated with the conductive polymer blend or nanocomposite making up the matrix. The conductive plate is electrically coupled to the matrix and the terminal, and can span an entire surface of the matrix. In some embodiments, the conductive plate has an area comparable or equal to that of the planar surface of the matrix facing the outside of the cassette, and is parallel to this surface. Thus, the conductive plate can facilitate uniform current flow through the entire mass of the matrix, and in turn facilitate the uniform transfer of biological species during electroblotting.

In a kit comprising two conductive polymer electrodes, each with a cassette encasing the matrix, the lips of the cassettes can be positioned to engage each other when the electrodes are brought together. For example, notches in the lip of one cassette can align with grooves in the lip of the other cassette. Alternatively, the lips of the two cassettes can have protruding or indented portions, in some cases running around the entire circumference of the cassette, that fit inside each other or interlock. Engagement of the lips of the cassettes can prevent one electrode from undergoing rotational or lateral movement with respect to the other electrode during electroblotting, and/or prevent the electrodes from separating. In some embodiments, the lip of one cassette is complementary in shape to the lip of the other cassette, so that engagement of the lips of the cassettes secures the electrodes together while leaving a gap between the matrices. The gap can accommodate an electrophoresis gel and blotting membrane between the matrices and any porous membranes during electroblotting.

Figure 4:
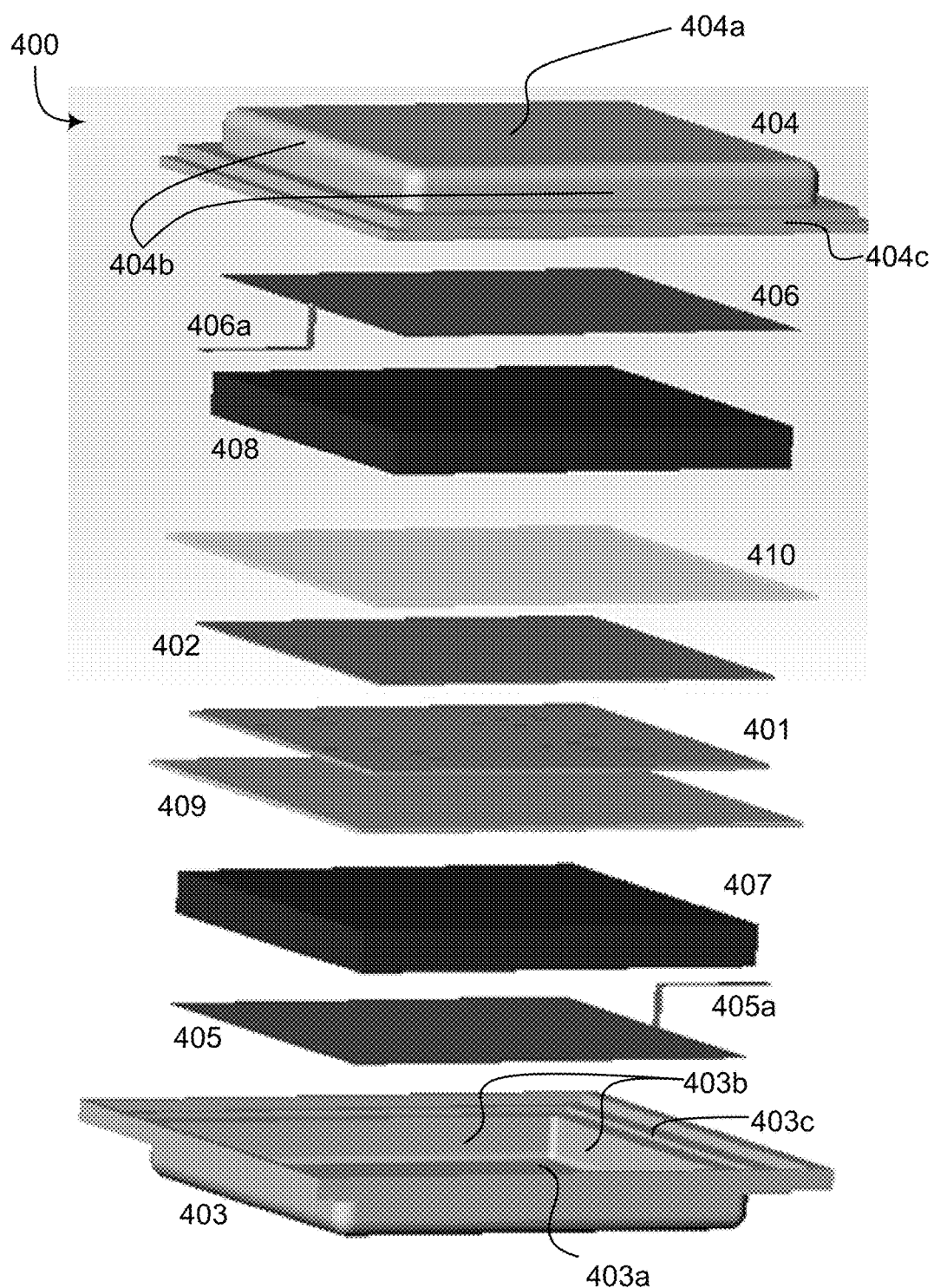
FIG. 4 is an exploded view of two conductive polymer electrodes according to some embodiments of the invention, and a electrophoresis slab gel and blotting membrane to be accommodated in a gap between the electrodes.
Figure 5:
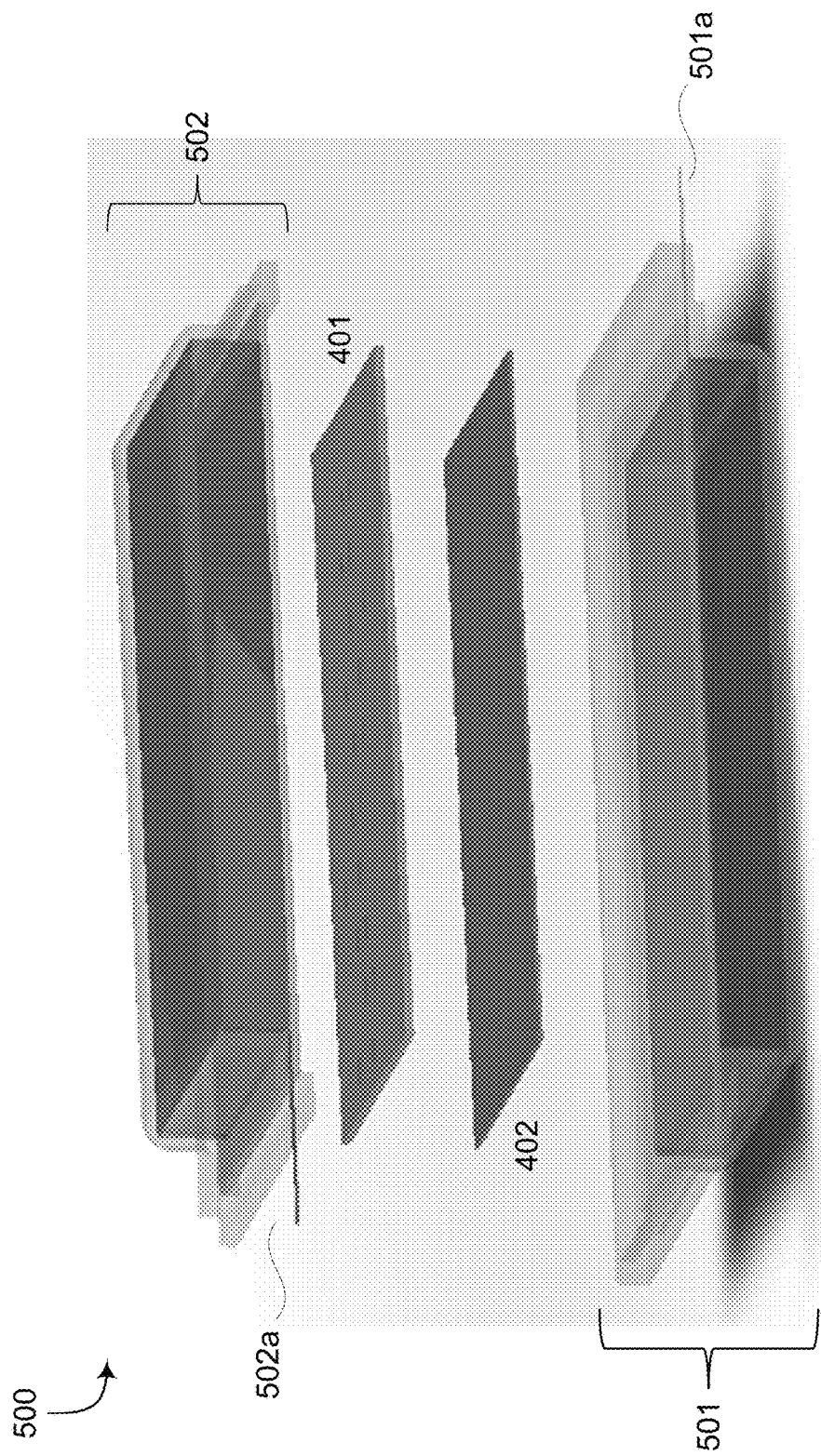
FIG. 5 shows the conductive polymer electrodes of FIG. 4 in fully assembled form.

Features of cassettes according to some embodiments of the invention can be appreciated by making reference to FIGS. 4 and 5. FIG. 4 is an exploded view 400 of two conductive polymer electrodes with an electrophoresis gel 401 and blotting membrane 402 sandwiched in between. Each conductive polymer electrode includes a rigid cassette 403, 404 with a floor 403a, 404a, walls 403b, 404b connected to the floor, and a lip 403c, 404c extending laterally from the walls. A conductive plate 405, 406 is disposed on the floor of each cassette. Each conductive plate has an elongated portion 405a, 406a that extends away from the floor and leads to the space outside the cassette. The elongated portion can electrically couple to or serve as a terminal for receiving electrical power. In each conductive polymer electrode, a matrix 407, 408 comprising a conductive polymer blend is disposed in the central cavity defined by the floor and walls of the cassette. The matrix is electrically coupled to the conductive plate through the surface of the matrix closest to the floor of the cassette. This surface is approximately parallel to a planar surface that interfaces with the electrophoresis gel or blotting membrane and faces the outside of the cassette. Each matrix is separated from the electrophoresis gel and blotting membrane by a porous membrane 409, 410. When the conductive polymer electrodes are brought together, the lips of the cassettes engage each other, thereby securing the electrodes together while leaving a gap between the matrices. The gap accommodates the electrophoresis gel and blotting membrane.

FIG. 5 is a sectional view of a kit according to embodiments of the invention, where the conductive polymer electrodes are separated from each other. FIG. 5 shows the conductive polymer electrodes of FIG. 4 fully assembled, and aligned with (but separated from) the electrophoresis gel 401 and blotting membrane 402. Each electrode 501, 502 includes a rigid cassette, conductive plate, matrix, and porous membrane. The elongated portions 501a, 502a of the conductive plates extend from opposite sides of the cassettes and can be connected to a power supply (not shown). The electrodes can be brought together around the electrophoresis gel 401 and blotting membrane 402 for electroblotting.

Some embodiments of the cassettes described herein employ alignment pegs and holes in lieu of or in addition to lips with complementary shapes. In these embodiments, a plurality of alignment pegs protrude from the lip of the cassette of at least one electrode, and a plurality of alignment holes are cut into the lip of the cassette of at least one electrode (FIG. 3). Pegs can occur on one cassette and holes can occur on the other cassette, or pegs and holes can both occur on the same cassette. The alignment pegs and alignment holes are positioned to engage each other when the electrodes are brought together, and are complementary in shape to each other. Thus, engagement of the alignment pegs with the alignment holes secures the electrodes together while leaving a gap between the matrices. The alignment pegs and holes can serve the same purposes as lips of the cassettes having complementary shapes, for example to prevent movement or separation of the electrodes.

If desired, the alignment pegs can expand when inserted in the alignment holes to more effectively secure the electrodes together. Instead or in addition, the pegs or holes can be spring-loaded or have etched surfaces to increase friction. In some embodiments, an electrically insulating material is disposed on the surface of each alignment peg or lines the interior of each alignment hole. Thus, mechanical contacts between the cassettes are electrically insulated and conduction between the cassettes is prevented.

According to some embodiments of the present invention, kits include a clamp for securing the two conductive polymer electrodes together around an electrophoresis gel and a blotting membrane. The clamp can attach to the electrodes with any convenient geometry, and can be used in embodiments employing or lacking rigid cassettes to encase the matrices of the electrodes. When secured together with the clamp, the matrices of the electrodes face each other and are parallel; the electrophoresis slab gel and the blotting membrane are accommodated in a gap between the electrodes; and the clamp exerts force on the electrodes to keep each electrode in contact with either the electrophoresis slab gel or the membrane, and keep the electrophoresis slab gel and membrane in contact with each other. Any force effective to maintain an electrical path between the matrices of the electrodes, through the gel and blotting membrane, can be used. In embodiments employing cassettes, the electrodes can be secured together by the engagement of the cassette lips, or by the engagement of alignment pegs and holes as described above, and here the clamp can ensure that the electrodes remain so secured. In embodiments lacking cassettes, the clamp can contact the matrices directly and force them toward each other. Preferably, the clamp does not provide an alternative path for current between the electrodes, such that current is diverted from traveling through the gel and blotting membrane. The clamp can accordingly be made in whole or in part of nonconducting materials such as plastics. In some embodiments, however, the clamp is electrically coupled to the terminal of each electrode and is configured to deliver electrical power to the terminals from the power supply. Thus, the clamp can serve the dual purposes of mechanically securing the electrodes together and conducting current toward and away from the electrodes.

Embodiments of the kits can also include a power supply. Any power supply can be used that, when electrically coupled to the conductive polymer electrodes described herein, is effective to cause electroblotting of biological macromolecules. The power supply is configured to deliver electrical power to the electrodes through the terminals, wherein the current delivered to one electrode is of opposite polarity from the current delivered to the other electrode. Examples of suitable power supplies are those in the PowerPac™ product line sold by Bio-Rad Laboratories, Inc. (Hercules, Calif., USA).

III. Systems

Systems are also provided herein for transferring biological macromolecules from an electrophoresis slab gel to a blotting membrane by electroblotting. A system can include a pair of conductive polymer electrodes and a power supply as described above, as well as a gel and a blotting membrane.

Any electrophoresis gel can be used in the systems described herein. For example, the gel can be of any dimensions, have any number of lanes, and be prepared (poured) by hand or by machine. In some embodiments, the gel comprises polyacrylamide or agarose, which can be present at any percentage or concentration, including at more than one concentration (e.g. in stacking and resolving portions of the gel) or at a gradient of concentrations. The gel can also comprise a denaturing agent such as sodium dodecyl sulfate or urea, as well as buffering agents such as tris(hydroxymethyl)aminomethane (Tris), glycine, or tricine. Other common constituents of electrophoresis gels, particularly gels used to separate proteins or nucleic acids, will be apparent to the skilled artisan.

In some embodiments, the gel includes additives that allow proteins to migrate through the gel faster and at higher applied voltages than would be practicable in the absence of these additives. The additives also improve separation of proteins by preventing the duplication of bands, which can result from gaps or undesired interactions between the gel and the container in which it is held (see e.g. U.S. Pat. No. 7,056,426). Examples of such additives include poly(vinyl alcohol), agarose, poly(vinyl pyrrolidone), poly(ethylene glycol), poly(ethylene oxide), poly(propylene glycol), poly(propylene glycol)/poly(ethylene glycol) copolymers, and linear polyacrylamide. Electrophoresis gels containing one or more of these additives are available from Bio-Rad under the name 'TGX'.

In some embodiments, the gel also includes a halo-substituted organic compound such as trichloroethanol or trichlororacetate as a constituent. This compound can react in situ with tryptophan residues of proteins in the gel, resulting in a detectable fluorescent product. The reaction, and the associated reagents, apparatus, and methods used to perform the reaction and detect products thereof, are sometimes referred to by the name 'Stain-Free™' (Bio-Rad).

Prior to electroblotting, biological macromolecules can be separated within the gel by performing electrophoresis or "running" the gel. This can be done using any techniques desired, and using any available materials or apparatus. In standard practice, the gel is contacted with the electrode buffer(s) and placed between two electrodes, which are energized to opposite polarities. The resulting electric field between the electrodes drives electrophoresis. Proteins or other macromolecules that have been loaded in the gel migrate within the gel, away from the site of loading, and become separated from each other according to molecular weight, size, or charge. Electrophoresis can also separate macromolecules from contaminants that may have been loaded onto the gel as part of a biological sample. Such contaminants can fail to enter the gel when the potential difference is applied, can diffuse from the gel into the surrounding buffer, or can pass through the gel more slowly or quickly than macromolecules of interest. For convenience and if desired, a molecular weight marker can be loaded into the gel along with a biological sample, allowing the practitioner to track the positions of macromolecules during or after migration.

In some embodiments, electrophoresis and electroblotting are performed using separate systems or apparatus. For example, electrophoresis can be performed with the gel retained in one apparatus, and the gel can then be removed from that apparatus and inserted between the conductive polymer electrodes of the present systems for electroblotting.

The present systems can also make use of any blotting membrane for electroblotting. Standard blotting membranes are made of nitrocellulose, nylon, or polyvinylidene fluoride (PVDF). It will be recognized that the most appropriate blotting membrane for use in a particular system depends on the type of biological macromolecules to be transferred, the composition of the electrophoresis gel, the details of any detection scheme to be performed after transfer, or other considerations. In some embodiments, the blotting membrane is sized at least as large as the slab gel, so that any biological macromolecules distributed in the gel, regardless of their locations, can be transferred to the blotting membrane.

In the present systems, the electrophoresis gel and blotting membrane are accommodated in a gap between the electrodes. This gap can result from protrusions in any rigid cassettes included in the electrodes, as described above. The power supply is configured as described above to deliver electrical power to the electrodes through the terminals, wherein the current delivered to one electrode is of opposite polarity from the current delivered to the other electrode. With the electrophoresis gel and blotting membrane sandwiched between the electrodes, current delivered through the terminals can flow between the electrodes, passing through the gel and membrane and facilitating electroblotting. The system is further configured to transfer biological macromolecules from the electrophoresis slab gel to the membrane, in the absence of an exogenous source of buffer, electrolyte, or solvent in contact with the electrophoresis slab gel or membrane, upon delivering electrical power to the electrodes. Efficient transfer can occur in a fully dry configuration, with any necessary liquids and electrolytes originating only from the gel, in part because electrochemical reactions are less prevalent at surfaces of the conductive polymer electrodes as compared with conventional metal electrodes.

In some embodiments, the systems also include a clamp, as described above, for securing the two electrodes together around the electrophoresis slab gel and blotting membrane. When the electrodes are so secured, the matrices of the electrodes face each other and are parallel, and the clamp exerts force on the electrodes to keep each electrode in contact with either the electrophoresis slab gel or the blotting membrane, and keep the electrophoresis slab gel and blotting membrane in contact with each other. The clamp thus ensures that current can travel between the matrices of the electrodes while passing through the electrophoresis slab gel and blotting membrane. Preferably, when the electrodes are secured with the clamp, the area of contact between the matrix of each electrode and either the electrophoresis slab gel or the blotting membrane is maximized, and the area of the gel or blotting membrane over which current can flow and biological macromolecules can be transferred is in turn maximized. This can be achieved by applying force evenly over the areas of the electrode matrices, or using the clamp in conjunction with electrode cassettes that engage each other through complementarily shaped lips or alignment pegs and holes. If desired, the clamp can be electrically coupled to the terminal of each electrode and be configured to deliver electrical power to the terminals from the power supply.

IV. Methods

Embodiments of the present invention also include methods for transferring biological macromolecules from an electrophoresis slab gel to a blotting membrane by electroblotting. Biological macromolecules, also called biological species herein, that can be transferred using the present kits, systems, and methods include but are not limited to proteins, nucleic acids, lipids, carbohydrates, and variants thereof (for example, post-translationally modified proteins, glycosylated proteins, native proteins, denatured proteins, antibodies, antibody fragments, protein-small molecule conjugates, protein-nucleic acid conjugates, DNA, and RNA). Such biological macromolecules can be naturally occurring, chemically synthesized, or chemically modified.

Methods can be carried out using any of the conductive polymer electrodes described above. The matrices of two conductive polymer electrodes can be positioned to face each other, such that each electrode is in contact with either the electrophoresis slab gel or the blotting membrane, and the electrophoresis slab gel and blotting membrane are in contact with each other. The electrophoresis slab gel and blotting membrane can be accommodated in a gap between the electrodes as described above. With the terminals of the electrodes connected to a power supply, electrical power can be delivered to the electrodes through the terminals, wherein the current delivered to one electrode is of opposite polarity from the current delivered to the other electrode. Biological macromolecules are thus transferred from the electrophoresis slab gel to the blotting membrane by electroblotting.

In some embodiments, the progress of electroblotting is monitored by tracking the current or potential difference between the terminals of the electrodes. This can be done using the digital display of the power supply, for example. The current or voltage can rise, fall, or fluctuate as the conductive polymer blend in each electrode undergoes oxidation or reduction. Accordingly, power can be applied to the electrodes until the current or voltage reaches a predetermined level (for example, falls below or rises above a threshold level). In some embodiments, power is applied at constant voltage until the current falls below a threshold level. In some embodiments, power is applied at constant current until the voltage surpasses a threshold level.

Alternatively or in addition, the progress of electroblotting can be monitored by visualizing the color of the electrode matrices, which can change over time due to electrochromism. For example, in PEDOT:PSS electrodes, dark or light blue color can indicate reduced or oxidized PEDOT, respectively. Accordingly, power can be applied in the present methods until one electrode attains a desired color, or the two electrodes attain distinguishable colors. These colors can be determined qualitatively or quantitatively, as desired. For example, the color of an electrode matrix can be determined quantitatively by measuring the amount of light absorbed, transmitted, or reflected by the matrix (or a portion thereof) at a desired wavelength. To visualize the colors of the electrode matrices, a portion of any enclosure around each matrix, such as a rigid cassette, can be configured to be transparent.

Prior to electroblotting, the conductive polymer blends of the two electrodes can have the same, similar, or different oxidation states. For example, one electrode (such as the cathode) can be initially oxidized and the other electrode (such as the anode) can be initially reduced. The initial oxidation states of the electrodes can be established as desired, for example during preparation of the electrode matrices. Without being bound by theory, the flow of current during electroblotting causes free electrons to migrate from the anode to the cathode through the power supply, and positively charged electrolytes (such as sodium ions) to migrate from the matrix of the anode to the matrix of the cathode through the electrophoresis slab gel and blotting membrane. The conjugated organic polymer in the anode can become more positively charged as it is oxidized, and associate more strongly with a polyelectrolyte or other counterion. In some embodiments, the anode is in contact and electrically interfaces with the electrophoresis slab gel during electroblotting. In other embodiments, the anode contacts and interfaces with the blotting membrane during electroblotting. Appropriate placements of the electrophoresis slab gel and blotting membrane with respect to the anode and cathode depend on the charges (if any) carried by the biological macromolecules to be transferred during electroblotting.

Standard procedures can be carried out before electroblotting to separate or distribute biological macromolecules within the electrophoresis gel. Similarly, standard procedures can be used to detect biological macromolecules on the blotting membrane after electroblotting.

In some embodiments, the electrodes are reconditioned to reverse changes in the oxidation states of the electrodes that occur during electroblotting. Reconditioning can be performed after electroblotting by placing a blank electrophoresis gel or other conductive, electrolyte-containing medium between the electrodes and running current between the electrodes in a direction opposite to that used for electroblotting. Alternatively, reconditioning can be performed during recurrent uses of the electrodes. For example, the power supply can be configured so that the direction of current flow during each electroblotting procedure is the opposite of that used for the previous procedure. Thus, an electrode that is oxidized in one procedure can be reduced in the next procedure and vice versa. The orientation of the electrophoresis gel and blotting membrane between the electrodes can be switched as appropriate to ensure that productive electroblotting of biological macromolecules from the electrophoresis gel to the blotting membrane occurs in every procedure. Reconditioning can increase the number of electroblotting procedures for which a pair of conductive polymer electrodes can be used, and prolong the useful lives of the electrodes.

In some embodiments, the electrodes are pre-conditioned to optimize the oxidation states of the electrodes prior to electroblotting. For example, a blank electrophoresis gel can be placed between the electrodes, and current can be flowed between the electrodes so that one electrode is fully oxidized and one is fully reduced. The oxidation states of the electrodes can be monitored using changes in the current or voltage, or using electrochromism, as described above. The blank electrophoresis gel can then be substituted with an electrophoresis gel containing biological macromolecules and a blotting membrane. To achieve electroblotting, current can then be flowed between the electrodes in a direction opposite that used for pre-conditioning. A pre-conditioning step can increase the amount of current that can flow between two conductive polymer electrodes during electroblotting.

As desired, a pair of conductive polymer electrodes can be used in one execution of the present methods, or in multiple executions. Single-use (i.e., disposable) electrodes can provide convenience by eliminating the need to clean or recondition electrodes after electroblotting. Thus, using a new pair of electrodes for every electroblotting procedure can lead to time and/or energy savings at the point of use. Provided that each pair of electrodes is prepared consistently, with regard to the initial oxidation states and compositions of the matrices, among other factors, single-use electrodes can also provide better reproducibility between electroblotting procedures than multi-use electrodes. On the other hand, multiple-use electrodes can provide cost savings. In some embodiments, conductive polymer electrodes are configured to have replaceable matrices, so that single-use matrices can be installed in a multi-use cassette, for example.

The present methods also include securing the two electrodes together in some embodiments. The electrodes can be secured, for example, using a clamp or features of rigid cassettes encasing the matrices, as described above. In some embodiments, no exogenous source of buffer, electrolyte, or solvent is in contact with the electrophoresis slab gel or blotting membrane.

V. Example

Two conductive polymer electrodes were constructed from Petri dishes and used to carry out electroblotting of proteins.

A rectangular through-hole was cut in the floor of each Petri dish and covered with a piece of nitrocellulose to serve as a porous membrane. The rectangular through-hole was surrounded by plastic baffles, which were perpendicular to the floor of the Petri dish and bonded together to define a cavity over the nitrocellulose. The cavity was filled with an aqueous dispersion of PEDOT:PSS (1.3 percent by weight) and the end of a wire was submerged in the dispersion. 3 nm LAPONITE® particles were then added to the dispersion to form a thixotropic nanocomposite.

The two Petri dishes were placed together such that the floors of the Petri dishes faced each other and the pieces of nitrocellulose were aligned. An electrophoresis gel containing stained proteins, already separated by electrophoresis, was placed between the Petri dishes along with a blotting membrane. The wires in the cavities were connected to a power supply and current was passed between the conductive polymer electrodes, thus causing proteins to be transferred from the electrophoresis gel to the blotting membrane. After electroblotting, the stained proteins were visible on the blotting membrane.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A kit for transferring biological macromolecules from an electrophoresis slab gel to a blotting membrane by electroblotting, the kit comprising two conductive polymer electrodes, wherein each electrode comprises:
    a matrix comprising a conductive polymer blend, the conductive polymer blend comprising a conjugated organic polymer, and
    a terminal electrically coupled to the matrix, wherein the terminal is configured to receive electrical power from a power supply,
    wherein:
    each electrode further comprises a rigid cassette encasing the matrix, the cassette comprising a floor, walls connected to the floor, and a lip extending laterally from the walls;
    the floor and walls of the cassette define a central cavity; and
    the matrix is disposed in the central cavity, and
    either of:
    (a) the terminal of each electrode is disposed on an external surface of the cassette and is electrically coupled to the matrix through a conductive member, the conductive member passing through a wall of the cassette or the floor of the cassette; or
    (b) a plurality of alignment pegs protrude from the lip of the cassette of at least one electrode,
    a plurality of alignment holes are cut into the lip of the cassette of at least one electrode,
    the alignment pegs and alignment holes are positioned to engage each other when the electrodes are brought together, and
    the alignment holes are complementary in shape to the alignment pegs, so that engagement of the alignment pegs with the alignment holes secures the electrodes together while leaving a gap between the matrices.

2. The kit of claim 1, wherein the conjugated organic polymer is a polythiophene, polyaniline, polypyrrole, polyphenylene, or poly(p-phenylene vinylene).

3. The kit of claim 2, wherein the conjugated organic polymer is poly(3,4-ethylenedioxythiophene) (PEDOT).

4. The kit of claim 1, wherein the conductive polymer blend further comprises a polyelectrolyte.

5. The kit of claim 4, wherein the conjugated organic polymer is positively charged and the polyelectrolyte is negatively charged.

6. The kit of claim 4, wherein the polyelectrolyte is water-soluble.

7. The kit of claim 4, wherein the polyelectrolyte is a sulfonated polystyrene.

8. The kit of claim 4, wherein the conductive polymer blend comprises poly(3,4-ethylenedioxythiophene):poly(styrenesulfonate) (PEDOT:PSS).

9. The kit of claim 1, wherein the conductive polymer blend is water-soluble.

10. The kit of claim 1, wherein the matrix is a nanocomposite.

11. The kit of claim 10, wherein the matrix further comprises a synthetic clay.

12. The kit of claim 1, wherein the matrix is thixotropic.

13. The kit of claim 1, wherein the terminal of each electrode is disposed on an external surface of the cassette and is electrically coupled to the matrix through a conductive member, the conductive member passing through a wall of the cassette or the floor of the cassette.

14. The kit of claim 1, wherein the lips of the cassettes are positioned to engage each other when the electrodes are brought together, and the lip of one cassette is complementary in shape to the lip of the other cassette, so that engagement of the lips of the cassettes secures the electrodes together while leaving a gap between the matrices.

15. The kit of claim 1, wherein:
- a plurality of alignment pegs protrude from the lip of the cassette of at least one electrode,
- a plurality of alignment holes are cut into the lip of the cassette of at least one electrode,
- the alignment pegs and alignment holes are positioned to engage each other when the electrodes are brought together, and
- the alignment holes are complementary in shape to the alignment pegs, so that engagement of the alignment pegs with the alignment holes secures the electrodes together while leaving a gap between the matrices.

16. The kit of claim 1, further comprising a clamp for securing the two electrodes together around an electrophoresis slab gel and a blotting membrane, such that, when the electrodes are so secured:
- the matrices of the electrodes face each other and are parallel;
- the electrophoresis slab gel and the blotting membrane are accommodated in a gap between the two electrodes; and
- the clamp exerts force on the electrodes to keep each electrode in contact with either the electrophoresis slab gel or the blotting membrane, and keep the electrophoresis slab gel and blotting membrane in contact with each other.

17. The kit of claim 1, further comprising a power supply configured to deliver electrical power to the electrodes through the terminals, wherein the current delivered to one electrode is of opposite polarity from the current delivered to the other electrode.

18. A system for transferring biological macromolecules from an electrophoresis slab gel to a blotting membrane by electroblotting, the system comprising:
- the two conductive polymer electrodes of the kit of claim 1;
- an electrophoresis slab gel and a blotting membrane accommodated in a gap between the electrodes; and
- a power supply configured to deliver electrical power to the electrodes through the terminals, wherein the current delivered to one electrode is of opposite polarity from the current delivered to the other electrode,
- wherein the system is configured to transfer biological macromolecules from the electrophoresis slab gel to the blotting membrane, in the absence of an exogenous source of buffer, electrolyte, or solvent in contact with the electrophoresis slab gel or blotting membrane, upon delivering electrical power to the electrodes.

19. A method for transferring biological macromolecules from an electrophoresis slab gel to a blotting membrane by electroblotting, wherein:
- the electrophoresis slab gel and the blotting membrane are accommodated in a gap between the two conductive polymer electrodes of the kit of claim 1, such that each electrode is in contact with either the electrophoresis slab gel or the blotting membrane, and the electrophoresis slab gel and blotting membrane are in contact with each other, and
- the terminals of the electrodes are connected to a power supply, the method comprising:
delivering electrical power to the electrodes through the terminals, wherein the current delivered to one electrode is of opposite polarity from the current delivered to the other electrode,
thereby transferring biological macromolecules from the electrophoresis slab gel to the blotting membrane by electroblotting.

* * * * *